United States Patent
Reinhardt et al.

(10) Patent No.: US 10,036,721 B2
(45) Date of Patent: Jul. 31, 2018

(54) METHOD FOR OPERATING A SOLID ELECTROLYTE SENSOR ELEMENT CONTAINING A PUMP CELL

(71) Applicant: Robert Bosch GmbH, Stuttgart (DE)

(72) Inventors: Goetz Reinhardt, Boeblingen (DE); Hartwig Lehle, Stuttgart (DE); Bernhard Ledermann, Stuttgart (DE)

(73) Assignee: ROBERT BOSCH GMBH, Stuttgart (DE)

( * ) Notice: Subject to any disclaimer, the term of this patent is extended or adjusted under 35 U.S.C. 154(b) by 56 days.

(21) Appl. No.: 14/440,972

(22) PCT Filed: Sep. 20, 2013

(86) PCT No.: PCT/EP2013/069614
§ 371 (c)(1),
(2) Date: May 6, 2015

(87) PCT Pub. No.: WO2014/072112
PCT Pub. Date: May 15, 2014

(65) Prior Publication Data
US 2015/0293052 A1 Oct. 15, 2015

(30) Foreign Application Priority Data
Nov. 12, 2012 (DE) .................. 10 2012 220 567

(51) Int. Cl.
*G01N 27/41* (2006.01)
*G01N 27/406* (2006.01)
(Continued)

(52) U.S. Cl.
CPC ......... *G01N 27/41* (2013.01); *F02D 41/146* (2013.01); *F02D 41/1454* (2013.01); *G01N 27/407* (2013.01); *G01N 27/4065* (2013.01)

(58) Field of Classification Search
CPC ............... G01N 27/406–27/41; G01N 33/0004–33/0075; F02D 41/1452; F02D 41/1454; F02D 41/146
See application file for complete search history.

(56) References Cited

U.S. PATENT DOCUMENTS

| | | | |
|---|---|---|---|
| 4,609,453 A | * | 9/1986 | Shimomura ......... G01N 27/417 204/412 |
| 7,585,402 B2 | | 9/2009 | Farber |

(Continued)

FOREIGN PATENT DOCUMENTS

| | | |
|---|---|---|
| CN | 101329371 A | 12/2008 |
| CN | 102959393 A | 3/2013 |

(Continued)

OTHER PUBLICATIONS

Leonard Mordfin, Handbook of reference data for nondestructive testing, 2002, p. 87.*

(Continued)

Primary Examiner — Maris R Kessel
Assistant Examiner — Joshua L Allen
(74) Attorney, Agent, or Firm — Norton Rose Fulbright US LLP; Gerard Messina

(57) ABSTRACT

A method is described for operating a sensor element for detecting at least one concentration of a gas in a measuring gas chamber. The sensor element includes at least one pump cell having at least two pump electrodes connected to each other by at least one solid electrolyte. At least one measuring variable is detected in the method, and at least one compensating variable is determined. The compensating variable is at least partially dependent on capacitive effects on at least one junction between at least one of pump electrodes and the solid electrolyte. At least one corrected measuring variable is determined from the measuring variable and the compensating variable. The concentration of the gas in the measur- (Continued)

ing gas chamber is determined from the corrected measuring variable.

6 Claims, 2 Drawing Sheets

(51) Int. Cl.
  *F02D 41/14* (2006.01)
  *G01N 27/407* (2006.01)

(56) References Cited

U.S. PATENT DOCUMENTS

| | | | | |
|---|---|---|---|---|
| 2004/0045823 | A1* | 3/2004 | Kawase | G01N 27/419 204/424 |
| 2005/0284772 | A1* | 12/2005 | Farber | G01N 27/4065 205/775 |
| 2012/0199478 | A1* | 8/2012 | Sasaki | G01N 27/4065 204/406 |

FOREIGN PATENT DOCUMENTS

| | | |
|---|---|---|
| DE | 10 2007 061947 | 6/2009 |
| DE | 10 2010 000663 | 7/2011 |
| DE | 10 2010 031060 | 1/2012 |
| DE | 10 2010 040817 | 3/2012 |
| DE | 10 2010 042695 | 4/2012 |
| DE | 10 2011 005648 | 9/2012 |
| JP | S60-135855 A | 7/1985 |
| JP | 2000-002686 A | 1/2000 |
| JP | 2003-329637 A | 11/2003 |
| JP | 2004-093289 A | 3/2004 |
| JP | 3925379 B2 | 6/2007 |
| JP | 2009-500594 A | 1/2009 |
| JP | 5832156 B2 | 12/2015 |
| WO | 2014072112 A1 | 5/2014 |

OTHER PUBLICATIONS

Meizhong Wang, Understandable Electric Circuits, 2010, p. 254.*
"Sensoren im Kraftfahrzeug [Sensors in a Motor Vehicle]'" Konrad Reif, Springer-Vieweg 2. Edition, 2012, pp. 160-165.

* cited by examiner

METHOD FOR OPERATING A SOLID ELECTROLYTE SENSOR ELEMENT CONTAINING A PUMP CELL

FIELD OF THE INVENTION

The field of the invention relates to a method for operating a solid electrolyte sensor element containing a pump cell.

BACKGROUND INFORMATION

Sensor elements and methods for operating the sensor elements for determining at least one concentration of a gas in a measuring gas chamber are known from the related art. Without limiting further possible embodiments, the present invention is described hereafter essentially with reference to methods and devices which are used to quantitatively and/or qualitatively detect at least one concentration of at least one gas component in the gas, in particular in a gas mixture. The gas mixture may be an exhaust gas of an internal combustion engine, for example, in particular in the automobile sector. The measuring gas chamber may be an exhaust system, for example. The sensor element may be a Lambda probe, for example. As an alternative, the sensor element may also be an $NO_x$ sensor. Lambda probes are described in Robert Bosch GmbH: Sensoren im Kraftfahrzeug [Sensors in the Motor Vehicle], 1st edition 2010, pages 160-165, for example. The gas component may in particular be oxygen and/or nitrogen and/or at least one nitrogen oxide and/or at least one hydrocarbon and/or another type of gas component. Sensor elements of the described type may in particular be based on the use of one or multiple solid electrolytes, i.e., on the use of solids, in particular ceramic solids, which have ion-conducting, in particular oxygen ion-conducting, properties. Examples of such solid electrolytes are zirconia-based solid electrolytes, such as yttria-stabilized zirconia (YSZ) and/or scandium-stabilized zirconia (ScSZ). Lambda probes generally operate according to the principle of a pump cell. The concentration of the gas may be an oxygen partial pressure and/or an oxygen concentration and/or a volume percent of oxygen. The usually linear correlation of a limit current with an oxygen partial pressure may be used, for example, to carry out a measurement of the oxygen partial pressure in the exhaust gas.

In the case of broadband lambda probes, also referred to as broadband lambda sensors, for example, a quantity of $O_2$ or fat gas diffusing in a measuring cavity is measured either based on a limit current, which may be in single-cell sensors, in particular in the LSP (proportional lambda probe), or based on a pump current which is necessary to regulate a cavity concentration to lambda=1 and which may then also correspond to a limit current, for example in dual-cell sensors, in particular in the LSU (universal lambda probe). A flowing pump current, in particular in the form of a measuring current, is usually proportional to the $O_2$ content in the exhaust gas and/or to the fat gas concentration in the exhaust gas.

A pump voltage necessary for electrochemical reactions and ohmic losses in the solid electrolyte is usually ensured by a so-called Nernst control in a dual-cell sensor. In a single-cell sensor, the pump voltage is usually adjusted to the pump current with the aid of a linear ramp or multiple ramps, for example having different slopes. This is referred to as pump voltage adjustment, for example.

The methods and devices from the related art are believed to have have several disadvantages. For example, a charge of a double layer capacitance of an inner pump electrode (IPE) is reversed in the case of the pump voltage adjustment for single-cell sensors. The resulting charge-reversal currents are usually observable as overshoots and/or undershoots in a probe signal, for example in the limit current, when the concentration of gas in the measuring gas chamber changes, for example in the case of changes in the exhaust gas composition, and result in signal errors, for example. When the changes of the gas in the measuring gas chamber are rapid, for example in the case of rapid gas exchanges, these signal errors may be particularly pronounced and may cause many applications which require high dynamics of the probe signal not to be operable, for example. A method and a device which at least to some extent mitigate the disadvantages known from the related art would therefore be desirable.

SUMMARY OF THE INVENTION

Accordingly, a method and a device are introduced, which at least largely avoid the disadvantages of known methods and devices. The device according to the present invention includes at least one sensor element for detecting at least one concentration of a gas in a measuring gas chamber. In principle, the sensor element may be any arbitrary device which is configured to detect the concentration of the gas in the measuring gas chamber. The sensor element may be a lambda probe, for example a single-cell sensor and/or a dual-cell sensor. In principle, the sensor element may also be an $NO_x$ sensor and/or a broadband lambda probe. For example, the sensor element may be a lambda probe, as described in Robert Bosch GmbH: Sensoren im Kraftfahrzeug [Sensors in the Motor Vehicle], 1st edition 2010, pages 160-165. The sensor element may be a ceramic sensor element. The detection may in principle be a quantitative and/or qualitative detection. The gas may in principle be any arbitrary gas. The gas particularly may be an exhaust gas of an internal combustion engine. The concentration of the gas may be a concentration and/or a percentage and/or a partial pressure and/or a volume percent of at least one gas component of the gas, for example. The gas component may be oxygen and/or $NO_x$, and/or a nitrogen oxide and/or a hydrocarbon, for example. The gas may include at least one gas component. The measuring gas chamber may in principle be any arbitrary chamber which is configured to receive the gas. The measuring gas chamber may be an exhaust system. For example, the measuring gas chamber may be a chamber in which the gas is situated.

The sensor element includes at least one pump cell having at least two pump electrodes connected to each other by at least one solid electrolyte. The pump cell may generally be any arbitrary electrochemical cell which includes at least two pump electrodes and the solid electrolyte. The cell may be operated in a pumping mode. The solid electrolyte may in particular be a ceramic solid. The solid electrolyte may have ion-conducting, in particular oxygen ion-conducting, properties. Examples of such solid electrolytes are zirconia-based solid electrolytes, such as yttria-stabilized zirconia (YSZ) and/or scandium-stabilized zirconia (ScSZ). A pump cell may in particular be a cell through which an ion current may flow and/or through which an ion current may be driven. On the pump electrodes of the pump cell, conversions from an ion current into an electron current and/or vice versa may take place, for example with the aid of oxidation and/or reduction. The pump electrodes may be composed at least partially of at least one conductive material, for example at least one metallic material. A conversion of an ion current into an electron current may take place on at least one surface of a pump electrode. Among the pump electrodes, a first pump electrode, for example an outer pump electrode, may be exposable to the gas mixture. A second pump electrode may be situated in a cavity, for example separated from the gas by at least one porous diffusion barrier and/or by the solid electrolyte. The cavity may be connected to an exhaust duct. For example, the cavity may also be connected to a further chamber, for example at least one reference gas chamber, via a further diffusion barrier and/or via the solid electrolyte. The second pump electrode may be at least one inner pump electrode, for example.

The pump electrodes may thus include at least one first pump electrode and at least one second pump electrode, for example. The first pump electrode and/or the second pump electrode may in principle be configured like a pump electrode, such as that described above. The designations "first" and "second" serve merely as descriptions and in particular provide no information about an order or, for example, whether the pump electrodes include further pump electrodes, for example at least one third pump electrode. The device may include, for example, at least one further pump electrode and/or at least one further electrode, which may be at least one reference electrode. For example, the reference electrode may be situated at least partially in at least one reference gas channel. The expression "exposable to the gas mixture" may be understood to mean, for example, that the gas mixture may be supplied to the first pump electrode, in particular directly, but also indirectly, for example, which may be via at least one porous layer, for example via at least one porous protective layer. The diffusion barrier may be understood to mean, for example, a layer made up of a material which suppresses a flow of the gas and/or of a fluid and/or of the gas mixture and/or of the gas component, while the layer promotes a diffusion of the gas and/or of the fluid and/or of the gas mixture and/or of the gas component and/or of ions. The cavity may be understood to mean a chamber inside the sensor element which is structurally separated from the measuring gas chamber, but to which nonetheless the gas component and/or the gas mixture and/or the gas from the measuring gas chamber may be supplied, for example via at least one gas access path and/or via the diffusion barrier. For example, the cavity may also be supplied with gas and/or with the gas component only via the solid electrolyte. The exhaust duct may be a connection to the ambient air, for example, in particular in order to prevent overpressure in the cavity.

As an alternative, the first pump electrode may be an inner pump electrode and the second pump electrode may be an exhaust duct electrode. The inner pump electrode may be situated in the cavity. The inner pump electrode may be supplied with gas via the diffusion barrier. The exhaust duct electrode may be connected at least partially to air, which may be ambient air, via the exhaust duct.

The device includes at least one control unit. The control unit is configured to carry out a method according to the present invention for operating the sensor element, as described hereafter. The control unit and/or the device may include at least one data processing device. For example, the data processing device may be integrated into the control unit. However, the data processing device may also be situated at least partially separated from the control unit, for example. The control unit and/or the data processing device may be connected and/or connectable to the sensor element, for example. The control unit may be understood to mean a device which is configured to support and/or control at least one function of the device, in particular of the sensor element. "Connectable" may be understood to mean, for example, a characteristic in which an electrical connection may be established or already exists. The control unit may be configured entirely or partially separately from the sensor element; however, it may also be entirely or partially integrated into the sensor element, for example into at least one plug of the sensor element and/or the device. The control unit may include at least one voltage measuring device and/or at least one current measuring device for detecting at least one pump current and/or at least one pump voltage and/or at least one limit current and/or for regulating the pump voltage and/or for regulating the pump current.

The control unit particularly may at least partially include at least one pump voltage adjustment unit. The pump voltage adjustment unit may be configured, for example, to adjust the pump voltage to the pump current in a single-cell sensor. As an alternative or in addition, the control unit and/or the sensor element and/or the device may include at least one application device and/or at least one pump voltage adjustment unit. The application device may include in particular at least one voltage source and/or at least one current source. For example, the application device may be configured to apply the pump current and/or the pump voltage to the sensor element and/or to at least partially implement the pump voltage adjustment.

In a further aspect of the present invention, a method for operating a sensor element for the detection of at least one concentration of a gas in a measuring gas chamber is introduced. The sensor element may be a sensor element as described above. The sensor element includes at least one pump cell having at least two pump electrodes connected to each other by at least one solid electrolyte. In the method, at least one measuring variable is detected. The measuring variable may in principle be any arbitrary physical and/or chemical variable. The measuring variable may be at least one measuring signal of the sensor element. The measuring variable may be at least one pump current $I_p$, for example a limit current. For example, the measuring variable may be a variable dependent on the pump current. For example, the measuring variable may be a pump voltage and/or a converted charge. The expression "being detected" may be understood to mean that the measuring variable is output as a measuring signal, for example, by the sensor element and/or the measuring variable is processed and/or evaluated and/or stored by the control unit.

In the method, moreover at least one compensating variable is determined. The compensating variable may in principle be understood to mean any arbitrary chemical and/or physical variable. The compensating variable may include the same physical and/or chemical variable as the measuring variable. The compensating variable may be a pump current deviation $\Delta I_p$. For example, the compensating variable may be at least one charge-reversal current and/or at least one electrode charge reversal. The compensating variable is at least partially dependent on capacitive effects on at least one junction between at least one of the pump electrodes and the solid electrolyte. For example, the compensating variable may be a measure of a distortion of the measuring variable by capacitive effects on at least one junction between at least one of the pump electrodes and the solid electrolyte. The capacitive effects may include charging processes and/or discharging processes, for example. The junction may be a double layer, for example. For example, the junction may be a junction from the solid electrolyte, which may be via a gas, to the pump electrode. The capacitive effects may be effects, for example, which may take place since the junction may be described as a parallel circuit made up of at least one capacitor and at least one resistor changing with the composition of the gas. The capacitive effects may be effects which may take place in circuits which include at least one capacitor and at least one resistor. For example, the capacitive effects may be charging and/or discharging effects of capacitances, for example capacitors and/or capacitor-like elements. For example, a junction from the solid electrolyte to the gas and/or a junction from the pump electrode to the gas may be described as and/or understood to mean "plates" of an electrical capacitor. The junction between at least one of the pump electrodes and the solid electrolyte may in particular be a solid electrolyte/gas phase/electrode junction.

At least one corrected measuring variable is determined from the measuring variable and the compensating variable. The corrected measuring variable may in principle be any arbitrary chemical and/or physical variable. The corrected measuring variable may be the same physical and/or chemical variable as the measuring variable and/or the compensating variable. The corrected measuring variable may in particular be a variable which has been adjusted for interfering effects. The concentration of the gas in the measuring gas chamber may be determined with greater precision from the corrected measuring variable than from the measuring variable. The determination of the corrected measuring variable from the measuring variable and the compensating variable may be a calculation and/or an assignment, for example. The concentration of the gas in the measuring gas chamber is determined from the corrected measuring variable. The concentration of the gas in the measuring gas chamber may be determined from the corrected measuring variable by calculation and/or by assignment, for example. For example, at least one characteristic may be used when determining the concentration of the gas in the measuring gas chamber from the corrected measuring variable. The characteristic may be an assignment of the corrected measuring variable to a concentration of the gas, for example. For example, the characteristic may be an assignment between a corrected pump current and a concentration of oxygen in the gas, for example an oxygen partial pressure.

The measuring variable may include at least one pump current Ip. For example, the pump current may be the entire charge converted across the pump cell per time. For example, the measuring variable may directly be the pump current. For example, the pump current may also be a measuring variable which depends on the pump current. For example, the measuring variable may be a variable dependent on the pump current. For example, the measuring variable may include at least the pump current. The compensating variable may include at least one charge-reversal current ΔIp. The charge-reversal current may be currents which may occur due to charging processes and/or discharging processes, for example during changes in the concentration of the gas in a measuring gas chamber. The charge-reversal current may be currents which may occur during capacitive charging processes and/or capacitive discharging processes. For example, the pump cell and/or at least one of the pump electrodes may be described as a parallel circuit of at least one capacitor and at least one resistor, the resistance being able to change when the concentration of the gas changes, in particular with regard to the magnitude of an ohmic resistance. It is possible to calculate the corrected measuring variable $Ip_{korr}$, for example from the measuring variable and the compensating variable. The corrected measuring variable may be a variable which may only include the number of charge carriers per time across the pump electrode which result from converted gas and/or are proportional to the converted gas. The corrected measuring variable and/or the measuring variable and/or the compensating variable may be electrochemical variables. The corrected measuring variable may be calculated from the measuring variable and the compensating variable by at least one subtraction. The subtraction may be a weighted subtraction, for example. In principle, the corrected measuring variable may be calculated and/or generated from the measuring variable and the compensating variable, for example by using any arbitrary mathematical function and/or assignment. The corrected measuring variable may be determined in particular using the formula $Ip_{korr}=Ip-\Delta Ip$.

The method may be carried out at least partially by at least one control unit, for example by the control unit as described above. The control unit may include at least one application-specified integrated circuit (ASIC), for example. The method may be carried out at least partially by the data processing device, for example. The method may be carried out, for example, with every detection of the concentration of the gas in the measuring gas chamber; however, it may also be repeated at least once at arbitrary time intervals. For example, the compensating variable may be stored, for example in a memory, which may be in a memory of the control unit. For example, the compensating variable may be used multiple times during the detection of the concentration of the gas in the measuring gas chamber, for example for multiple measuring variables, which may be detected at different times.

In the method, at least one characteristic curve over time of at least one voltage across at least one electrochemical double layer $U_{dL}(t)$ may be determined. In the method, which may be at least one derivative of the characteristic curve over time of the voltage across the electrochemical double layer $$\frac{\partial U_{dL}}{\partial t}$$

may be determined. The characteristic curve over time may be a continuous characteristic curve over time of the voltage across the electrochemical double layer. For example, the characteristic curve over time may also be a characteristic curve including discrete values for the voltage across the electrochemical double layer at different times. The characteristic curve over time may include at least two values for the voltage across the electrochemical double layer $U_{dL}$, for example. The derivative may be a first order derivative, particularly may be a first order derivative with respect to time t. When determining the derivative of the characteristic curve over time of the voltage across the electrochemical double layer $$\frac{\partial U_{dL}}{\partial t},$$

at least one arithmetic operation, which may be a differential calculus, may be carried out. The derivative of the characteristic curve over time of the voltage across the electrochemical double layer may be a slope in the characteristic curve over time of the voltage across the electrochemical double layer, for example. The electrochemical double layer may in particular be a junction, as described above. In the method, at least one charge-reversal current ΔIp may be determined as the compensating variable using the characteristic curve over time of the voltage across the electrochemical double layer $U_{dl}(t)$, particularly may be the derivative of the characteristic curve over time of the voltage across the electrochemical double layer $$\frac{\partial U_{dL}}{\partial t}$$

and at least one electrode capacitance $C_{IPE}$, in particular using the formula $$\Delta Ip = \frac{\partial Q}{\partial t} = C_{IPE} \frac{\partial U_{dl}}{\partial t},$$

where $$\frac{\partial Q}{\partial t}$$

may denote a derivative of an electrical charge with respect to time. The charge-reversal current $\Delta Ip$ may in particular be a capacitive charge-reversal current. The electrode capacitance may in particular be an electrical capacitance of the junction between the pump electrode and the solid electrolyte, which may be the electrochemical double layer. The electrode capacitance may be a ratio of a charge Q, which is stored at the pump electrode and/or at the solid electrolyte, to a voltage U present between them. The electrode capacitance may change over time, for example due to aging effects. For example, the electrode capacitance may decrease by a factor of 2 to 5, in particular by a factor of 3, due to aging, for example over the service life of the sensor element. Electrode capacitance $C_{IPE}$ may be stored and/or storable in the control unit, for example. For example, electrode capacitance $C_{IPE}$ may be a variable measured during production and/or an estimated variable and/or a known variable. For example, electrode capacitance $C_{IPE}$ may be determined in the method according to the present invention.

The pump cell may be operated in pulsed mode, for example. The pump cell may be operated in pulsed mode by the control unit, for example. The pump cell and/or the sensor element may particularly be operated in pulsed mode by pulse width modulation. Pulse pauses may take place between voltage pulses and/or current pulses. The pulse pause may in particular be a phase in the operation of the sensor element during which no electric current is present at the pump cell. The pump cell may be operated in pulsed mode in particular in such a way that a square wave voltage and/or a square wave current is/are applied to the pump cell. The characteristic curve over time of the voltage across the electrochemical double layer $U_{dl}(t)$ may be detected by measurement in at least two different pulse pauses. As an alternative or in addition, the derivative of the characteristic curve over time of the voltage across the electrochemical double layer $$\frac{\partial U_{dl}}{\partial t} = \frac{Up_j - Up_i}{\Delta t_{i,j}}$$

may be detected by measurement in at least two different pulse pauses. The pulse pause may in particular be a pulse pause of a pulse width modulation. During the measurement in at least two different pulse pauses, in particular a voltage Up may be measured and/or a variable which depends on the voltage, for example an electric current and/or an ohmic resistance. For example, at least one ith and at least one jth pulse pause may be used at a time interval of $\Delta t_{i,j}$. i and j may be integers, i≠j being preferred. For example, at least one pump voltage may be detected during the ith pulse pause $Up_i$, and at least one pump voltage may be detected during the jth pulse pause $Up_j$. Using the formula $$\frac{\partial U_{dl}}{\partial t} = \frac{Up_j - Up_i}{\Delta t_{i,j}},$$

for example at least one derivative, which may be as defined above, of the characteristic curve over time of the voltage across the electrochemical double layer $$\frac{\partial U_{dl}}{\partial t}$$

may be determined. The pulse pauses i and j may be contiguous pulse pauses, for example in particular j=n and i=n−1 may apply.

As an alternative or in addition, at least one change over time of at least one pump current $$\frac{\Delta Ip}{\Delta t}$$

may be detected. For example, at least one change over time of at least one pump voltage $$\frac{\Delta Up}{\Delta t}$$

may be determined. The change over time of the pump voltage may be determined using the formula $$\frac{\Delta Up}{\Delta t} = \frac{(\Delta Up_{setpoint} \cdot (1 - \exp(-\Delta t/\tau)))}{\Delta t}.$$

$Up_{setpoint}$, which may be may $$\frac{\Delta Up_{setpoint}}{\Delta t},$$

may be calculated in the course of a pump voltage adjustment, for example by the control unit, in particular when the change, for example an approximately step-shaped change, of the concentration of the gas in the measuring gas chamber is significant and/or rapid. This formula, in particular its exponential component, in particular takes into consideration a weakening of the pump voltage due to the use of a low-pass filter. The low-pass filter may be included in the control unit and/or in the device, for example, which may be in order to suppress an oscillating behavior of a regulating unit.

Using the change over time of the pump current $$\frac{\Delta Ip}{\Delta t}$$

and the change over time of the pump voltage $$\frac{\Delta Up}{\Delta t},$$

and at least one ohmic resistance of at least a portion of the solid electrolyte $R_{Electrolyte}$, for example at least one derivative, which may be as defined above, of the characteristic curve over time of the voltage across the electrochemical double layer $$\frac{\partial U_{dl}}{\partial t}$$

may be calculated, in particular using the formula $$\frac{\partial U_{dl}}{\partial t} = \frac{\Delta Up}{\Delta t} - R_{electrolyte}\frac{\Delta Ip}{\Delta t}.$$

$\Delta t$ may in principle be freely selected. $\Delta t$ may be selected in such a way that both the pump current Ip and the pump voltage Up essentially change linearly over this time segment $\Delta t$. The ohmic resistance of at least a portion of the solid electrolyte $R_{Electrolyte}$ may be stored, for example, in the control unit and/or may be detected in the method, for example by applying a current and measuring the voltage and/or by applying a voltage and measuring the current. At least one derivative, which may be as defined above, of the characteristic curve over time of the voltage across the electrochemical double layer $$\frac{\partial U_{dl}}{\partial t}$$

may be calculated from the difference of the change in the pump voltage $$\frac{\Delta Up}{\Delta t}$$

during the pump voltage adjustment, taking into consideration the low-pass filter and the voltage dropping across the ohmic resistance of at least one portion of the solid electrolyte $R_{Electrolyte}$.

In the method, at least one electrode capacitance $C_{IPE}$ may be detected. In principle, electrode capacitance $C_{IPE}$ may be stored and/or storable in the device, for example in a memory of the control unit. Electrode capacitance $C_{IPE}$ may be detected during every detection of the concentration of the gas in the measuring gas chamber, for example; however, it may also be detected once and stored in such a way that the electrode capacitance may be used multiple times, for example to detect the concentration of the gas in the measuring gas chamber and/or to determine the compensating variable.

For example, at least one pump voltage changing over time may be applied to the pump cell, in particular for detecting the electrode capacitance. At least one characteristic curve over time of at least one pump current may be detected. Electrode capacitance $C_{IPE}$ may be inferred from the characteristic curve over time of the pump current, in particular by evaluating at least one area and/or at least one integral of the pump current, for example as a current response.

The method according to the present invention and the device according to the present invention may have a plurality of advantages over known methods and devices. For example, a software compensation of capacitive charge-reversal currents may be carried out within the scope of the method according to the present invention and/or with the device according to the present invention. For example, signal deviations may be at least significantly reduced with a pump voltage adjustment. In this way, a signal accuracy may be ensured, in particular in the case of rapid gas changes, for example, and/or it may be ensured that it is also possible to apply dynamic system functions, for example when using the device according to the present invention and/or the method according to the present invention in a vehicle. The method according to the present invention and the device according to the present invention may furthermore result in a compensation of signal delays due to electrode charge reversal, which may also take place without pump voltage adjustment, for example.

Exemplary embodiments of the present invention are shown in the following figures and are described in greater detail in the following description.

DETAILED DESCRIPTION

Figure 1:
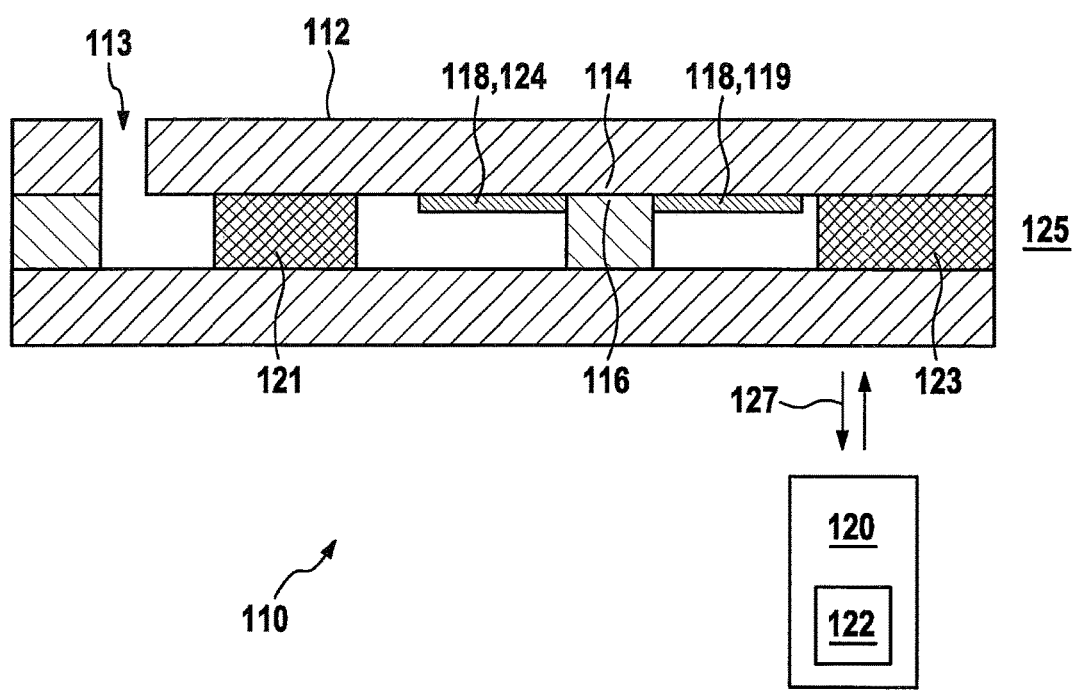
FIG. 1 shows one exemplary embodiment of a device according to the present invention.

FIG. 1 shows one exemplary embodiment of a device 110 according to the present invention. Device 110 includes at least one sensor element 112 for detecting at least one concentration of a gas, for example of an exhaust gas 113, in a measuring gas chamber. Sensor element 112 includes at least one pump cell 114 having at least two pump electrodes 118 connected to each other by at least one solid electrolyte 116. Device 110 includes at least one control unit 120. Control unit 120 may include at least one data processing device 122. Control unit 120 is configured to carry out a method according to the present invention. At least one of pump electrodes 118 may be an inner pump electrode (IPE) 124, for example. At least one of pump electrodes 118 may be an exhaust duct electrode 119, for example. Sensor element 112 may further include at least one diffusion barrier (DB) 121 and/or at least one exhaust duct (AK) 123. Exhaust duct electrode 119 may be at least partially connected to air 125 via exhaust duct 123. For example, at least a portion of exhaust gas 113 may reach inner pump electrode 118 via diffusion barrier 121. Inner pump electrode 118 and the exhaust duct electrode may be at least partially included in pump cell 114. Sensor element 112 may be a broadband lambda probe, in particular a broadband lambda probe having a pump cell 114. Sensor element 112 may be at least partially connected to control unit 120 and/or to data processing unit 122 via at least one interface 127.

Figure 2:
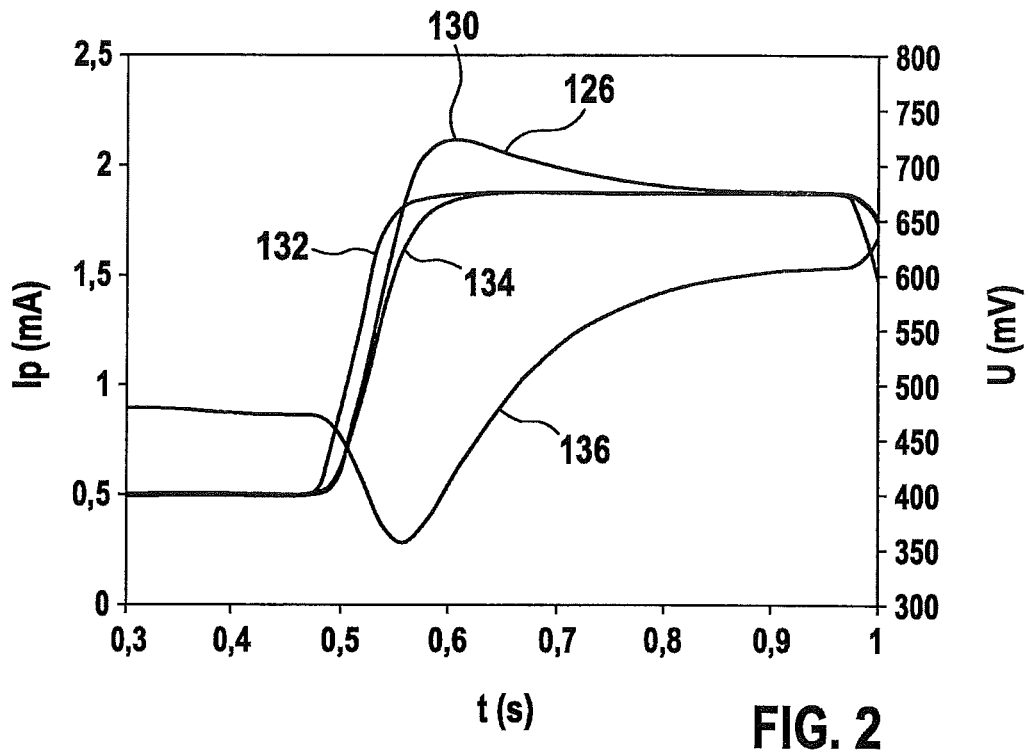
FIG. 2 shows a diagram for one exemplary embodiment of a method according to the present invention.
Figure 3:
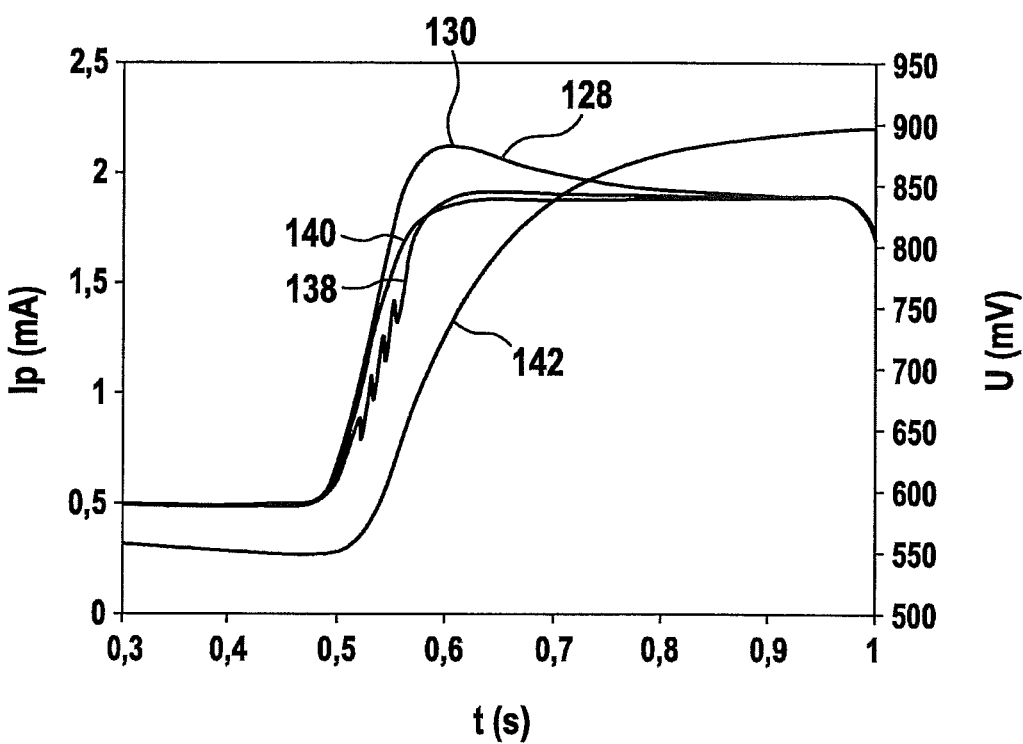
FIG. 3 shows a diagram for a further exemplary embodiment of a method according to the present invention.

FIGS. 2 and 3 show graphs for two different exemplary embodiments of the method according to the present invention.

Each graph shows pump currents Ip in mA, and voltages in mV, against a time t in s. The method according to the present invention is a method for operating a sensor element 112, for example as described above, for detecting at least one concentration of a gas in a measuring gas chamber. Sensor element 112 includes at least one pump cell 114 having at least two pump electrodes 118 connected to each other by at least one solid electrolyte 116. In the method, at least one measuring variable is detected. The measuring variable may be pump current Ip and/or voltage U, for example. Moreover, at least one compensating variable is determined. The compensating variable may be a compensating current $\Delta$Ip, for example. The compensating variable is at least partially dependent on capacitive effects on at least one junction between at least one of pump electrodes 118 and solid electrolyte 116. At least one corrected measuring variable is determined from the measuring variable and the compensating variable. The concentration of the gas in the measuring gas chamber is determined from the corrected measuring variable. For example, the concentration of the gas in the measuring gas chamber may be determined from the corrected measuring variable with the aid of at least one characteristic, for example a correlation between a pump current and the concentration of the gas in the measuring gas chamber.

The measuring variable may include at least one pump current Ip. The compensating variable may include at least one charge-reversal current $\Delta$Ip. The corrected measuring variable $Ip_{korr}$ may be calculated, in particular using the formula $Ip_{korr}$=Ip-$\Delta$Ip. The method may be carried out at least partially by at least one control unit, for example by a control unit 120 as described above. Control unit 120 may be an ASIC CJ135 or an ASIC CJ125, for example. For example, control unit 120 may include at least one ASIC CJ135 and/or at least one ASIC CJ125. In principle, the control unit may be any arbitrary control unit. The control unit may include at least one ASIC, for example at least one ASIC CJ125 and/or at least one ASIC CJ135 and/or at least one other ASIC.

In the method, at least one characteristic curve over time of at least one voltage across at least one electrochemical double layer $U_{dl}$(t) may be determined. In the method, which may be at least one derivative of the characteristic curve over time of the voltage across the electrochemical double layer $$\frac{\partial U_{dl}}{\partial t}$$

may be determined. For example, the voltage across the electrochemical double layer $U_{dl}$(t), in particular a voltage across the double layer capacitance, may be measured during operation, for example during a pulsed operation, in particular during a pulsed operation as with the use of an ASIC CJ135. For example, the voltage across the electrochemical double layer may also be alternatively determined and/or calculated, for example using a pump voltage adjustment unit. When using an ASIC CJ125, the use of the pump voltage adjustment unit may be indicated, for example, since the voltage, in particular the voltage across the electrochemical double layer, usually is not measurable. In principle, the voltage across the electrochemical double layer and/or the characteristic curve over time of the voltage across the electrochemical double layer and/or the derivative of the characteristic curve over time of the voltage across the electrochemical double layer $$\frac{\partial U_{dl}}{\partial t}$$

may alternatively or additionally be determined by alternative procedures. In the method, at least one, which may be a capacitive, charge-reversal current $\Delta$Ip may be determined as the compensating variable using the characteristic curve over time of the voltage across the electrochemical double layer, which may be the derivative of the characteristic curve over time of the voltage across the electrochemical double layer $$\frac{\partial U_{dl}}{\partial t}$$

and at least one electrode capacitance $C_{IPE}$, in particular using the formula $$\Delta Ip = \frac{\partial Q}{\partial t} = C_{IPE}\frac{\partial U_{dl}}{\partial t}.$$

A software compensation within the scope of the present invention may in particular be based on the measuring variable, for example the probe signal Ip, being corrected by a capacitive charge-reversal current $\Delta$Ip as the compensating variable. For example, the voltage $U_{dl}$ may be a voltage across an electrochemical double layer of at least one of pump electrodes 118, for example of at least one inner pump electrode 124, as is shown in FIG. 1, for example.

FIGS. 2 and 3 show in particular exemplary measuring variables, in particular pump currents Ip as lines 126 and 128. Lines 126 and 128 in each case have overshoots 130 in FIGS. 2 and 3. Overshoots 130 may be pump currents, for example, which are higher than a constant pump current which develops, for example following a change in the concentration of the gas in the measuring gas chamber. An area beneath overshoots 130, in particular between overshoots 130 and a constant pump current which develops after approximately 0.9 seconds, may be a variable for a flowed charge. For example, the area beneath overshoots 130 may be proportional to an electrode capacitance and to a change in the voltage: $\Delta Q=C_{IPE}\cdot\Delta U$.

In the exemplary embodiment of the method according to the present invention described in FIG. 2, pump cell 114 may be operated in pulsed mode, for example. Pulse pauses may take place between voltage pulses and/or current pulses. The characteristic curve over time of the voltage across the electrochemical double layer $U_{dl}$(t) may be detected by measurement in at least two different pulse pauses. The derivative of the characteristic curve over time of the voltage across the electrochemical double layer $$\frac{\partial U_{dl}}{\partial t}$$

may be detected by measurements in at least two different pulse pauses. For example, at least one ith and at least one jth pulse pause may be used at a time interval of $\Delta t_{i,j}$. At least one pump voltage may be detected during the ith pulse pause $Up_i$, and at least one pump voltage may be detected during the jth pulse pause $Up_j$. Using the formula $$\frac{\partial U_{dl}}{\partial t} = \frac{Up_j - Up_i}{\Delta t_{ij}},$$

at least one derivative, which may be as defined above, of the characteristic curve over time of the voltage across the electrochemical double layer $$\frac{\partial U_{dl}}{\partial t}$$

may be determined. This exemplary embodiment may be carried out using a digital ASIC CJ135 as control unit 120, for example. The digital ASIC CJ135 may be used to calculate compensating variable $\Delta Ip$ if capacitance $C_{IPE}$ is known, for example, since the voltage at the electrochemical double layer may correspond to the voltage during the pulse pause: $Udl(t)=Up(\text{pulse pause})$. The voltage during pulse pause $Up(\text{pulse pause})$, and thus voltage $Udl(t)$, may be measured during every clock pulse in the pulse pauses, for example. A change in the voltage, which may be for calculating the compensating variable, may be calculated with the aid of formula $$\frac{\partial U_{dl}}{\partial t} \approx \frac{(Up(\text{pulse pause } n) - Up(\text{pulse pause } n-1))}{\text{clock cycle}},$$

for example. The clock cycle may be $\Delta t_{n,n-1}$, for example, in particular the duration between the nth pulse pause and the n-lth pulse pause. In this exemplary embodiment, in particular a correction may be detected by detecting the change $$\frac{\Delta Up(\text{pulse pause})}{\Delta t},$$

which may be using at least one CJ135 as control unit 120. In this exemplary embodiment of the method according to the present invention, a current which is required for a charge reversal of a double layer capacitance may be directly corrected, for example, which may be by the compensating variable. This may have the positive side effect, for example, that also at least one signal delay may be compensated for by electrode charge reversal, which may also take place without pump voltage adjustment, for example, so that the corrected measuring variable, for example as a signal, may be even more dynamic with Up adjustment, also referred to as pump voltage adjustment, than without Up adjustment. FIG. 2 shows in particular a schematic illustration of the exemplary embodiment of the method according to the present invention, however in particular without the pulsed operation of the CJ135 as control unit 120 and without signal ripples occurring due to a stepped pump voltage adjustment; however, this should not change the basic procedure. This exemplary embodiment of the method according to the present invention may be used to at least partially, which may be completely, compensate for overshoot 130, for example provided that electrode capacitance $C_{IPE}$ and/or voltage curve $U_{dl}(t)$ are known and/or may be detectable precisely.

FIG. 2 shows in particular one exemplary embodiment of the method according to the present invention by correction via Up(pulse pause), for example in the case of a CJ135 as control unit 120. Line 132 shows in particular an exemplary characteristic curve of the corrected measuring variable, for example of $Ip_{korr}$. Line 134 shows pump current Ip without Up adjustment. Line 136 shows an exemplary characteristic curve of the pump voltage during pulse pauses Up(pulse pause)=U(IPE). The described overshoot 130 beneath line 126 is clearly discernible in FIG. 2. The areas between line 126 and line 134, in particular pump currents Ip with or without Up adjustment, correspond to the charge required for the electrode charge reversal. The described lines in FIG. 2 were generated by a simulation, for example, such as during a change in the concentration of the gas, in particular a gas exchange, for example from 6% to 21% oxygen ($O_2$).

In the further exemplary embodiment of the method according to the present invention associated with FIG. 3, at least one change over time of at least one pump current $$\frac{\Delta Ip}{\Delta t}$$

may be detected. For example, at least one change over time of at least one pump voltage $$\frac{\Delta Up}{\Delta t}$$

may be determined. Using the change over time of the pump current $$\frac{\Delta Ip}{\Delta t}$$

and the change over time of the pump voltage $$\frac{\Delta Up}{\Delta t},$$

and at least one ohmic resistance of at least a portion of solid electrolyte 116 $R_{electrolyte}$, for example at least one derivative, which may be as defined above, of the characteristic curve over time of the voltage across the electrochemical double layer $$\frac{\partial U_{dl}}{\partial t}$$

may be calculated, in particular using the formula $$\frac{\partial U_{dl}}{\partial t} = \frac{\Delta Up}{\Delta t} - R_{electrolyte} \frac{\Delta Ip}{\Delta t}.$$

In this further exemplary embodiment, an ASIC CJ125 may be used as control unit 120, for example. When the ASIC CJ125 is used, it is usually not possible to directly measure a change of the voltage dropping across the electrode double layer capacitance $$\frac{\partial U_{dl}}{\partial t}.$$

The voltage dropping across the electrode double layer capacitance, however, may at least be estimated from a change in the pump voltage, which may be calculated for the adjustment, in particular for the Up adjustment, in control unit 120, in particular in control unit ASIC CJ125. For this purpose, the entire change in pump voltage ΔUp may be reduced by the proportion which drops across solid electrolyte 116 as ohmic loss. The change in pump voltage ΔUp is obtained, for example, by detecting a change in Upsetpoint, for example ΔUpsetpoint, which may be calculated from a ramp for the pump voltage adjustment, taking a low-pass filter into consideration, for example a PT1 filter, as expressed in the following formula: ΔUp=ΔUpsetpoint·(1−$e^{(-\Delta t+96)}$). This further exemplary embodiment of the method according to the present invention may in particular be a correction via the change in the predefined pump voltage, which may be using at least one CJ125 as control unit 120. As is apparent from FIG. 3, overshoots 130, in particular signal overshoots, may be considerably reduced even when the change in the electrode double layer capacitance, for example in the electrode voltage, is estimated from the Up adjustment. FIG. 2 shows in particular that, as an alternative or in addition, overshoot 130 may also be significantly reduced by a correction via a change in the applied pump voltage, as is shown in line 138, for example. Line 138 shows in particular the corrected measuring variable, for example $Ip_{korr}$. Line 140 shows pump current Ip without adjustment. Line 142 shows pump voltage Up.

In one exemplary embodiment of the method according to the present invention, for example in one of the above-described exemplary embodiments, at least one electrode capacitance $C_{IPE}$ may be detected, for example in addition. In the method, for example, at least one pump voltage changing over time may be applied to pump cell 114. At least one characteristic curve over time of at least one pump current may be detected. Electrode capacitance $C_{IPE}$ may be inferred from the characteristic curve over time of the pump current. One prerequisite for one exemplary embodiment of the method according to the present invention may be that electrode capacitance $C_{IPE}$ is known or detectable, in particular for determining the compensating variable, for example of a compensating function. Since the value of the electrode capacitance may change drastically, for example due to aging, it may be advantageous to measure the electrode capacitance during operation, for example by carrying out the method according to the present invention. This may take place, for example, by applying a current to sensor element 112, in particular to a probe, which may be in limit current operation, and evaluating an area beneath a current response.

What is claimed is:

1. A method for operating a sensor element for detecting at least one concentration of a gas in a measuring gas chamber, the method comprising:
   detecting at least one measuring variable (Ip), the at least one measuring variable including a pump current of the sensor element, wherein the sensor element includes at least one pump cell having at least two pump electrodes connected to each other by at least one solid electrolyte;
   applying a chronologically changing pump voltage to the at least one pump cell;
   detecting a characteristic curve over time (t) of a resultant pump current resulting from the applied pump voltage;
   determining an electrode capacitance ($C_{IPE}$) wherein the electrode capacitance ($C_{IPE}$) is determined from the detected characteristic curve over time of the resultant pump current;
   determining a characteristic curve over time of a voltage across an electrochemical double layer ($U_{dl}$(t));
   determining a compensating variable (ΔIp) using 1) a derivative $$\frac{\partial U_{dl}}{\partial t}$$

of the determined characteristic curve over time of the voltage across the electrochemical double layer ($U_{dl}$(t)); 2) the electrode capacitance ($C_{IPE}$); and 3) the formula $$\Delta Ip = \frac{\partial Q}{\partial t} = C_{IPE}\frac{\partial U_{dl}}{\partial t}.$$

wherein $$\frac{\partial Q}{\partial t}$$

is a derivative of an electrical charge (Q) with respect to time, wherein the compensating variable (ΔIp) is dependent on the determined electrode capacitance ($C_{IPE}$);
   determining at least one corrected measuring variable ($Ip_{korr}$) from the at least one measuring variable (Ip) and the compensating variable (ΔIp), wherein the corrected measuring variable ($Ip_{korr}$) is calculated using the formula $Ip_{korr} = Ip - \Delta Ip$;

determining the concentration of the gas in the measuring gas chamber from the corrected measuring variable ($Ip_{korr}$) as a variable in the computation;
   outputting a measuring signal based on the corrected measuring variable ($Ip_{korr}$); and
   using the measuring signal in a vehicle.

2. The method of claim 1, wherein the method is at least partially carried out by at least one control unit.

3. The method of claim 1, wherein the at least one pump cell is operated in pulsed mode, pulse pauses take place in each case between voltage pulses and/or current pulses, and the characteristic curve over time of the voltage across the electrochemical double layer ($U_{dl}$(t)) is detected by measurement in at least two different pulse pauses.

4. The method of claim 3, wherein at least one ith and at least one jth pulse pause are used at a time interval of $\Delta t_{i,j}$, at least one pump voltage during the ith pulse pause $Up_i$ and at least one pump voltage during the jth pulse pause $Up_j$ are detected, and the derivative of the characteristic curve over time of the voltage across the electrochemical double layer $$\frac{\partial U_{dl}}{\partial t}$$

is determined using the formula $$\frac{\partial U_{dl}}{\partial t} = \frac{Up_j - Up_i}{\Delta t_{i,j}}.$$

5. The method of claim 1, wherein at least one change over time of at least one pump current $$\frac{\Delta IP}{\Delta t}$$

is detected, at least one change over time of at least one pump voltage $$\frac{\Delta Up}{\Delta t}$$

is determined, and using the change over time of the pump current $$\frac{\Delta IP}{\Delta t}$$

and the change over time of the pump voltage $$\frac{\Delta Up}{\Delta t},$$

and at least one ohmic resistance of at least a portion of the solid electrolyte ($R_{Electrolyte}$), the derivative of the characteristic curve over time of the voltage across the electrochemical double layer $$\frac{\partial U_{dl}}{\partial t}$$

is calculated.

6. The method of claim 1, wherein at least one change over time of at least one pump current $$\frac{\Delta Ip}{\Delta t}$$

is detected, at least one change over time of at least one pump voltage $$\frac{\Delta Up}{\Delta t}$$

is determined, and using the change over time of the pump current $$\frac{\Delta Ip}{\Delta t}$$

and the change over time of the pump voltage $$\frac{\Delta Up}{\Delta t},$$

and at least one ohmic resistance of at least a portion of the solid electrolyte ($R_{Electrolyte}$), the derivative of the characteristic curve over time of the voltage across the electrochemical double layer $$\frac{\partial U_{dl}}{\partial t}$$

is calculated, using the formula $$\frac{\partial U_{dl}}{\partial t} = \frac{\Delta Up}{\Delta t} - R_{Electrolyte} \frac{\Delta Ip}{\Delta t}.$$

* * * * *